United States Patent [19]

Tinti et al.

[11] Patent Number: 4,483,869

[45] Date of Patent: Nov. 20, 1984

[54] THIOCARNITINES, PROCESS FOR THEIR PREPARATION AND PHARMACEUTICAL COMPOSITIONS CONTAINING SAME

[75] Inventors: Maria O. Tinti; Emma Quaresima; Paolo de Witt, all of Rome, Italy

[73] Assignee: Sigma-Tau Industrie Farmaceutiche Riunite S.p.A., Rome, Italy

[21] Appl. No.: 330,998

[22] Filed: Dec. 15, 1981

[30] Foreign Application Priority Data

Dec. 24, 1980 [IT] Italy ................................ 50469 A/80

[51] Int. Cl.³ ...................... A01N 37/14; A01N 37/30; C07C 153/017; C07C 149/24
[52] U.S. Cl. ................................ 424/301; 260/455 R; 562/556; 424/316; 424/319
[58] Field of Search .................... 260/455 R; 562/556; 424/301, 316, 319

[56] References Cited

U.S. PATENT DOCUMENTS 2,217,846 10/1940 Orthner et al. ..................... 562/556

*Primary Examiner*—Henry R. Jiles
*Assistant Examiner*—Robert C. Whittenbaugh
*Attorney, Agent, or Firm*—Ladas & Parry

[57] ABSTRACT

A novel class of carnitine derivatives is disclosed which comprises thiocarnitine and the S-acyl thiocarnitines wherein the acyl radical is the radical of saturated organic acids having from 2 to 10 carbon atoms. The S-acyl thiocarnitines are prepared e.g. by reacting crotonoyl betaine halogenide with the corresponding thioacid, while thiocarnitine is obtained by hydrolysis of an S-acyl thiocarnitine. These compounds are useful therapeutic agents, e.g. for the treatment of intoxications, liver malfunctions and burns.

10 Claims, No Drawings

THIOCARNITINES, PROCESS FOR THEIR PREPARATION AND PHARMACEUTICAL COMPOSITIONS CONTAINING SAME

The present invention relates to a novel class of carnitine derivatives and, more particularly, it relates to thiocarnitine and the S-acyl derivatives of thiocarnitine wherein the acyl radical is the radical of saturated organic acids having from 2 to 10 carbon atoms, all these compounds being hereinbelow collectively indicated for brevity sake as "thiocarnitines". The present invention also relates to the processes for the preparation of such thiocarnitines and the terapeutical utilization thereof.

More specifically, the present invention relates to compounds having general formula:

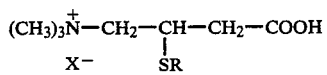 (I)

wherein:
$X^-$ is a pharmacologicaly acceptable halogenide ion, preferably the chloride ion, and
R is either hydrogen or the acyl radical of a saturated organic acid having from 2 to 10 carbon atoms.

This acyl radical is preferably selected from the group consisting of: acetyl, propionyl, butyryl, hydroxybutyryl, diethylacetyl, dipropylacetyl and acetoacetyl. Correspondingly, the preferred S-acyl thiocarnitines of the present invention are the following:
S-acetyl thiocarnitine halogenide;
S-propionyl thiocarnitine halogenide;
S-butyryl thiocarnitine halogenide;
S-hydroxy butyryl thiocarnitine halogenide;
S-diethylacetyl thiocarnitine halogenide;
S-dipropylacetyl thiocarnitine halogenide; and
S-acetoacetyl thiocarnitine halogenide.

A process for preparing thiocarnitines of formula (I) comprises the steps of:

(a) Reacting a solution of crotonoyl betaine halogenide,

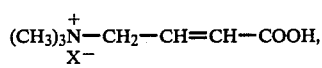

in an organic solvent with a thioacid of general formula R'COSH, wherein R' is such that R'CO=R, except the case wherein R=H, at a temperature comprised between about room temperature and about 80° C. for a period of time comprised between about 24 hours and about 72 hours, thus obtaining a thiocarnitine of formula (I) wherein R has the previously defined meaning with the exclusion of R=H; and (b) Optionally, if the thiocarnitine halogenide,

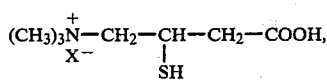

is desired as end product, hydrolyzing the thiocarnitine of step (a) in an acyl environment.

A suitable solvent for crotonoyl betaine halogenide consists of an excess of thioacid R'COSH. Alternatively, lower alkanols having from 1 to 4 carbon atoms, typically methanol and ethanol, can be used. In general, any organic solvent which is inert towards the reaction can be used. Preferably, the thioacid is slowly added in an atmosphere of inert gas (e.g. nitrogen) to the solution of crotonoyl betaine halogenide.

Catalysts, such as peroxy-compounds (e.g. m-chloro perbenzoic acid) or quaternary ammonium salts (e.g. benzyl trimethyl ammonium hydroxyde) or amines (e.g. triethylamine) can be advantageously used.

Crotonoyl betaine halogenide is a compound already known in the art. Its preparation is for instance disclosed in Biochimica et Biophysica Acta 137, 98 (1967) and in Arch. Biochem. Biophys. 38, 405 (1952), these articles being incorporated by reference in the present specification.

According to the foregoing prior art references, carnitine halogenide is dehydrated in an acid environment and in the presence of an dehydrating agent, at a temperature comprised between 90° and 100° C., for time periods comprised between about 2 and 24 hours, thus obtaining the desired compound. Suitable acid/dehydrating agent systems comprise acetic acid/acetic anhydride and trifluoracetic acid/trifluoracetic anhydride. Also sulfuric acid alone can be used.

Most of the thioacids R'COSH are compounds already known in the prior art. In case the thioacid is not already known, it can be then easily prepared by applying well-known procedures adjusting them to the preparation of the desired compound in such a way that will be apparent to anyone skilled in the art. Such thioacids are preferably prepared, according to the conventional procedures of the organic synthesis, starting from the corresponding acid chloride and reacting it with NaSH, as is for instance disclosed in Organic Synthesis Vol. IV, 924.

The following non-limiting examples illustrate the preparation and the chemico-physical characteristics of some compounds of the present invention.

EXAMPLE 1

Preparation of S-acetyl thiocarnitine hydrochloride

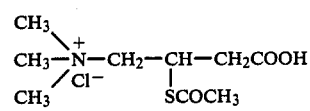

Crotonoyl betaine chloride (3.6 grams; 0.02 moles) was suspended in thioacetic acid (10 cc; 0.14 moles). The resulting reaction mixture was left to stand at room temperature under stirring for 3 days. Subsequently, the reaction mixture was poured in Et$_2$O, thus obtaining a precipitate. The raw product thus obtained was crystallized from warm isopropanol. The pure product thus obtained had melting point of 166°–168° C. Yield: 80%.

NMR δ 4.1 (m, 1H, —CH—); 3,8 (d, 2H, \+N—CH$_2$—);
          |
          S—

3.2 (s, 9H, CH$_3$—\+N\<); 2,9 (d, 2H, —CH$_2$—COOH);

2.4 (s, 3H, —S—COCH$_3$); D$_2$O

EXAMPLE 2

Preparation of S-dipropylacetil thiocarnitine hydrochloride

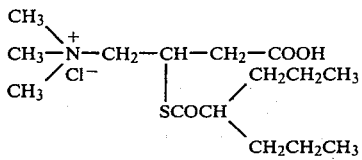

Crotonoyl betaine chloride (1.79 g; 0.01 moles) was dissolved in absolute ethanol (20 cc) and dipropyl-thioacetic acid (3.2 grams; 0.02 moles) and catalytic amounts of benzyl trimethyl ammonium hydroxyde were added to the resulting solution. The resulting reaction mixture was kept at 60° C. for 3 days and subsequently cooled to room temperature. Ethyl ether was then added thereto. The precipitate thus formed was filtered off and repeatedly crystallized with isopropanol/ethyl ether. A pure, solid compound was obtained having melting point 113°–115° C. Yield: 33%.

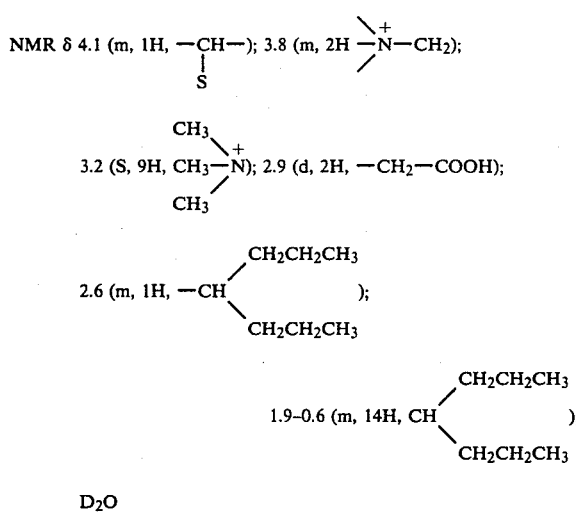

D$_2$O

EXAMPLE 3

Preparation of thiocarnitine hydrochloride

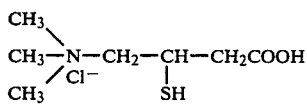

S-acetyl thiocarnitine hydrochloride (1.3 grams; 0.005 moles) prepared as described in example 1, was hydrolyzed by dissolving it in 2N HCl (10 cc) and keeping the resulting reaction mixture under stirring at 40° C. for 1 day. The reaction mixture was then evaporated to dryness under vacuum. The residue was taken up with isopropanol, filtered and dried under vacuum at 35° C. A product having melting point 168°–170° C. was obtained. Yield: 85%. The product was very hygroscopic and darkened upon exposure to the atmosphere.

NMR δ 3.50–3.87 (3H, m, —N⁺—CH$_2$—, —CH—);
                                            |
                                            SH

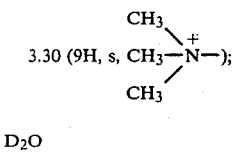

2.80–3.03 (2H, m, —CH$_2$CO—); D$_2$O

K.F. 4.5%

S %
Calculated    15.00
Found         14.24

In order to confirm the presence of the —SH group, the thiocarnitine hydrochloride thus obtained was acetylated. Thioacetyl carnitine hydrochloride was obtained, having chemico-physical characteristics identical to those of the starting compound.

An alternative way for preparing an S-acyl thiocarnitine, which is particulary preferred when the acyl radical has about 6–10 carbon atoms, comprises preparing first the S-acetyl thiocarnitine from crotonoyl betaine and thioacetic acid, then hydrolyzing the S-acetyl thiocarnitine thus obtaining thiocarnitine and lastly acylating thiocarnitine with the acid chloride, according to the well-known methods of the organic synthesis.

This preparation method, although indirect, allows the S-acyl thiocarnitine to be obtained with high yields and in the absence of catalysts, whereas it was observed that with the direct synthesis the yields decrease and the presence of the catalyst becomes more and more appropriate as the number of the carbon atoms of the acyl radical increases.

The last step of the indirect synthesis (i.e. the acylation of thiocarnitine to S-acyl carnitine) is illustrated in the following example 4.

EXAMPLE 4

Preparation of S-diethylacetyl thiocarnitine

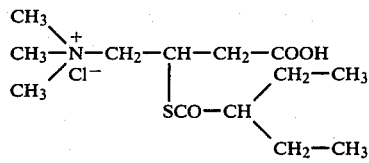

Thiocarnitine hydrochloride (1 gram; 0.005 moles) was dissolved in trifluoracetic acid (5 cc). To the solution diethylacetyl chloride (3.5 cc; 0.025 moles) was added. The resulting reaction mixture was kept under stirring at 45° C. for 3 days. Ethyl ether was added to the reaction mixture, the semi-solid precipitate thus obtained was separated and washed with ethyl ether in order to remove the excess of the ethylacetyl chloride.

The raw reaction product was crystallized from isopropanol-acetone. A highly hygroscopic, white, solid product was obtained, having melting point 115° C. Yield: 80%.

NMR δ 3.97–4.50 (1H, m, —CH—); 3.80 (2H, d, —N⁺—CH₂—);
           |
          SCO

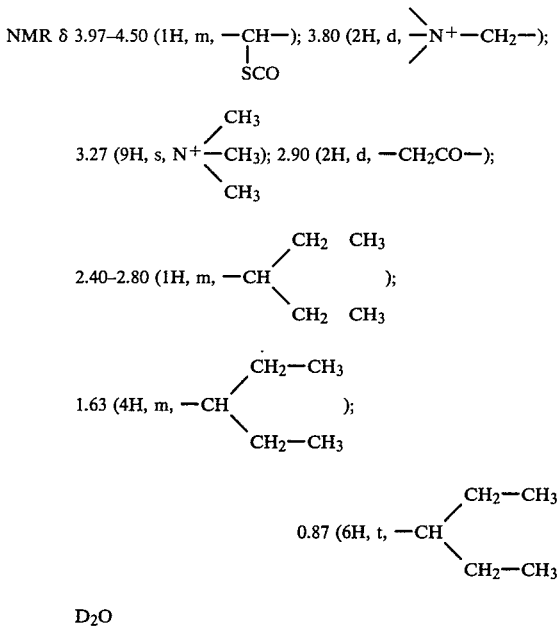

D₂O

A process other than that previously mentioned is advantageously utilized for preparing S-beta hydroxybutyryl thiocarnitine halogenide. Such process, in which S-acetoacetyl thiocarnitine forms as an intermediate product, is based on the reaction between thiocarnitine and diketene, thus obtaining S-acetoacetyl thiocarnitine which is hydrogenated, for instance, with sodium borohydride.

This process is illustrated in the following example 5.

EXAMPLE 5

Preparation of S-beta hydroxybutyryl thiocarnitine (a) Preparation of S-acetoacetyl thiocarnitine hydrochloride.

0.6 ml (0.0066 moles) of diketene were added dropwise under magnetic stirring to a solution of thiocarnitine (1 gram; 0.005 moles) in one ml of trifluoracetic acid, cooled with an ice bath. Upon termination of the addition, the reaction mixture was brought to room temperature and left to stand under stirring overnight. The reaction mixture was diluted with acetone, upon addition of ethyl ether raw S-acetoacetyl thiocarnitine hydrochloride precipitated which was crystallized from isopropanol-ethyl ether.

Analysis (C₁₁H₂₀ClNO₄S) C,H,N,Cl,S.

NMR (D₂O): 2.33 (3H, s, —COCH₃); 3.00 (2H, d, —CH₂COOH);

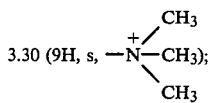

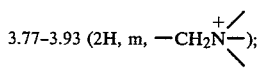

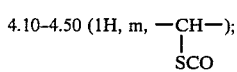

the δ concerning the protons of —SCOCH₂— is not reported because these protons exchange with D₂O.

(b) Hydrogenation of S-acetoacetyl thiocarnitine hydrochloride

To a solution of acetoacetyl thiocarnitine hydrochloride (1.25 grams; 0.0044 moles) in 26 ml of glacial acetic acid and 8.8 ml of absolute ethanol, cooled with an ice bath, 660 mg (0.017 moles) of NaBH₄ were added portionwise under stirring. After 2 hours, the reaction mixture was filtered and upon addition of ethyl ether a precipitate was obtained from the filtrate. The precipitate was taken up with isopropanol, brought to pH 2–3 with 1N HCl in isopropanol, then precipitated again with ethyl ether. The semisolid, very hygroscopic pure product was thus obtained.

Analysis (C₁₁H₂₂ClNO₄S) C,H,Cl,N,S.

NMR (D₂O) δ = 1.17 (3H, d, —CH—CH₃);
                          |
                          OH 2.77–3.00 (4H, m, —CH₂—COOH e —SCOCH₂—);

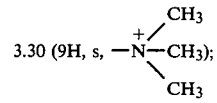

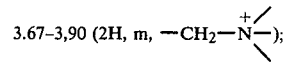

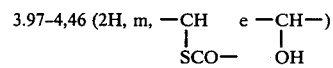

It has been found that the thiocarnitines of formula (I) are useful therapeutic agents for the treatment of intoxications and liver malfunctions, for the treatment of burns and the deseases of the epithelia and in general whenever it is important to restore to normal the metabolic cellular equilibrium unbalanced by exogenous and endogenous factors.

It is known that lack of sulphydryl groups SH available for the metabolism requirements, as well as the inability of the organism to utilize such groups in specific pathological situations, constitute the primary factor of anatomical and functional alterations of some body tissues. Indeed, the activity of most of the enzymes present in the cells of vital organs, such as liver, is related to the presence of SH groups in their molecules as well as to the activity of SH groups at the membrane level.

It is also known that the organism, when because of various reasons is unable to utilize the sulphydryl groups indispensable for the cellular metabolism to take place regularly, can utilize the sulphydryl groups that it derives from the administration of compounds containing such groups.

It has been difficult up to now to have available compounds able to cross the biologic membranes and free the SH groups in order to re-consititute the cellular membranes and restore the enzyme activity.

It has now been found that the compounds of the present invention possess a remarkable ability to cross the biologic membranes and particularly the mithocondrial membranes.

Moreover, in the case of S-acylthiocarnitines, the compounds provide, in addition to the SH groups, the energy related to the acyl groups (typically, acetyl) which is needed for essential metabolic processes to take place.

The characteristics of pharmacological activity of the compounds of general formula (I) are hereinbelow illustrated.

ACUTE TOXICITY

The acute toxicity of the compounds of general formula (I) has been studied in the mouse with the Weil method (Weil C. S., Biometr. J. 8, 249, 1952).

The LD50 values of some compounds illustrated in Table I, indicate that the compounds are remarkably well tolerated.

TABLE I

LD50, mg $Kg^{-1}$, ep in mouse of some thiocarnitines of general formula (I). Weil's method (N = 5, K = 4) Cl = hydrochloride

| Compounds | LD50 and fiducial limits | |
|---|---|---|
| Thiocarnitine $(CH_3)_3\overset{+}{N}—CH_2—\underset{\underset{SH}{\|}}{CH}—CH_2—COOH$ $Cl^-$ | 150 | 128– 162 |
| S—acetyl thiocarnitine Cl | 294 | 195– 443 |
| S—propionyl thiocarnitine Cl | 302 | 250– 354 |
| S—butyryl thiocarnitine Cl | 350 | 280– 420 |
| S—hydroxybutyryl thiocarnitine Cl | 300 | 262– 438 |
| S—diethylacetyl thiocarnitine Cl | 295 | 196– 444 |
| S—dipropylacetyl thiocarnitine Cl | 350 | 280– 420 |

PROTECTION AGAINST X-RAY EXPOSURE

The effect of the compounds of formula (I) towards the damages provoked by X-ray exposure was studied.

The experiment animals, Albino Wister rats, treated with the compounds under examination (20–25 mg $Kg^{-1}$ 1 hour before irradiation) were irradiated and checked over a time period to detect the onset of toxic effects and the time of survival with respect to the control group.

In table II, the percentages of survival at the 10th, 15th and 20th day from irradiation are reported.

TABLE II

Protective effect of some thiocarnitines of general formula (I) towards the damage provoked by irradiation in rats. Percentage of surviving animals at various days from irradiation.

| Compounds | Days of survival | | |
|---|---|---|---|
|  | 10 | 20 | 30 |
| Control | 90 | 20 | 10 |
| Thiocarnitine | 95 | 60 | 50 |
| S—acetyl thiocarnitine Cl | 100 | 70 | 60 |
| S—propionyl thiocarnitine Cl | 90 | 70 | 50 |
| S—butyryl thiocarnitine Cl | 90 | 40 | 40 |
| S—hydroxybutyryl thiocarnitine | 100 | 80 | 60 |
| S—diethylacetyl thiocarnitine Cl | 80 | 60 | 30 |
| S—dipropylacetyl thiocarnitine Cl | 90 | 70 | 50 |

CUTANEOUS REGENERATION

The ability of the compounds of formula (I) to speed up the cutaneous regeneration from burns has been tested in the rabbit.

A 4 $cm^2$ cutaneous area of the average-top zone of the test animal back was burned.

The compounds were orally administered in aqueous solution at the dose of 20 mg $Kg^{-1}$ once a day for seven days. The area of cutaneous regeneration i.e. the area of the newly formed tissue, was then measured (Table III).

TABLE III

Effect of compounds of formula (I) on cutaneous regeneration. Percentage of regenerated tissue at the 4th and 8th day from treatment.

| Compounds | Days | |
|---|---|---|
|  | 4th day | 8th day |
| Control | 20 | 50 |
| Thiocarnitine | 40 | 90 |
| S—acetyl thiocarnitine Cl | 50 | 90 |
| S—propionyl thiocarnitine Cl | 30 | 70 |
| S—butyryl thiocarnitine Cl | 20 | 40 |
| S—hydroxybutyryl thiocarnitine Cl | 30 | 60 |
| S—diethylacetyl thiocarnitine Cl | 50 | 60 |
| S—dipropylacetyl thiocarnitine Cl | 50 | 100 |

METABOLIC ACTIVITY TOWARDS ALCOHOL

The ability of the compounds of formula (I) to facilitate alcohol metabolism and act as liver detoxicants has been tested.

Albito Wistar rats received 6 grams of ethanol per Kg of body weight orally and were treated with the same compounds as those used in the previous tests at the dose of 20 mg $Kg^{-1}$ per os. At various time intervals from the treatment beginning the following parameters were checked:

(1) the alcohol content in blood;
(2) the alcohol content in the liver;
(3) the amount of liver triglycerides.

The results obtained show that the compounds facilitate the alcohol clearance from blood and liver and hinder the accumulation of liver triglycerides.

It has been also found that acetyl thiocarnitine promotes the formation of acetylcholine and is able to cross the blood-brain barrier. Since in the cerebral mitochondria the enzyme CoA carnitine acetyl transferase is very slightly active but acetyl thiocarnitine is able to transfer the acetyl group to CoA directly even in the absence of the enzyme, acetyl thiocarnitine acts as a potent acyl group donor. This is therapeutically relevant in the cases of lack of acetylcholine and when cerebral metabolism needs to be activated.

The scope of the present invention also encompasses a therapeutical method for the treatment of intoxications and liver malfunctions, for the treatment of burns and generally whenever it is important to restore to normal the metabolic cellular equilibrium unbalanced by exogenous and endogenous factors, which comprises orally or parenterally administering to patients in need thereof a therapeutically effective amount of thiocarnitine of general formula (I).

This method will generally comprise the oral or parenteral administration of about 2–20 mg/Kg of body weight/day of a thiocarnitine of general formula (I), although larger or smaller doses can be administered by the attending physician having regard to the age, weight and general condition of the patient, utilizing sound professional judgement.

In practice, the thiocarnitines (either as racemic mixture or as separate stereoisomers) are orally or parenterally administered, in any of the usual pharmaceutical forms which are prepared by conventional procedures well-known to those persons skilled in the pharmaceutical technology. These forms include solid and liquid oral unit dosage forms such as tablets, capsules, solutions, syrups and the like as well as injectable forms, such as sterile solutions for ampoules and phials. Some non-limiting examples of compositions suitable for the oral and parenteral administration are illustrated hereinbelow.

PHARMACEUTICAL PREPARATIONS

1. Solutions and sterile aqueous solutions containing the thiocarnitines of formula (I) in concentrations from 25 mg to 500 mg per ml.

(a) The excipient for injectable ampoules/phials is prepared in accordance with the following non-limitative composition:

| sodium carboxymethyl cellulose (at low viscosity) | 10 mg/ml |
|---|---|
| polysorbate 80 | 4 mg/ml |
| propylparaben | 0.4 mg/ml |
| water for injections sufficient for 1 ml, 2 ml, 5 ml and 10 ml ampoules/phials | |

(b) The excipient for phleboclysis bottles containing 50 ml, 100 ml, 250 ml, 500 ml and 1000 ml is prepared in accordance with the following non-limitative compositions:

| NaCl | 8.6 g/lt |
|---|---|
| KCl | 0.3 g/lt |
| CaCl$_2$ | 0.33 g/lt |
| water for injections sufficient for 1 liter. | |

(c) The excipient for bottles for oral use containing from 5 ml to 100 ml is prepared in accordance with the following non-limitative composition:

| mannitol | 11 mg/ml |
|---|---|
| sorbitol | 600 mg/ml |
| sodium benzoate | 3 mg/ml |
| orange extract | 200 mg/ml |
| vitamin B$_{12}$ | 3 mcg/ml |
| purified water | |

2. Tablets containing from 20 mg to 500 mg of the thiocarnitine of formula (I). The excipient is prepared in accordance with the following non-limitative composition:

| starch | 45% |
|---|---|
| avicel | 45% |
| talc | 10% |

3. Capsules containing from 20 mg to 500 mg of the thiocarnitines of formula (I) without excipients.

4. Aerosol and spray preparations from 50 mg to 10 g of thiocarnitines of formula (I). The excipient is prepared in accordance with the following non-limitative composition:

| ethanol | 30% |
|---|---|
| purified water | 30% |
| sufficient freon 12/114 (50 parts/50 parts). | |

What is claimed is:

1. Thiocarnitine of the formula

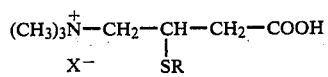  (I)

wherein:
X$^-$ is a pharmacologically acceptable halogenide ion, and
R is either hydrogen or the alkanoyl radical of a saturated organic acid having from 2 to 10 carbon atoms.

2. As thiocarnitine of claim 1, the thiocarnitine halogenide of formula

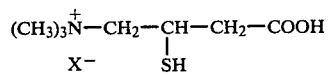

3. As thiocarnitine of claim 1, S-acetyl thiocarnitine halogenide.
4. As thiocarnitine of claim 1, S-propionyl thiocarnitine halogenide.
5. As thiocarnitine of claim 1, S-butyryl thiocarnitine halogenide.
6. As thiocarnitine of claim 1, S-hydroxy butyryl thiocarnitine halogenide.
7. As thiocarnitine of claim 1, S-diethyl acetyl thiocarnitine halogenide.
8. As thiocarnitine of claim 1, S-dipropylacetyl thiocarnitine halogenide.
9. A process for preparing thiocarnitines of the formula

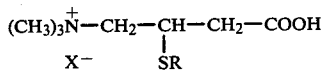  (I)

wherein:
X$^-$ is a pharmacologically acceptable halogenide ion, and
R is either hydrogen or the alkanoyl radical of a saturated organic acid having from 2 to 10 carbon atoms;
which comprises the steps of:
(a) reacting a solution of crotonoyl betaine halogenide in an organic solvent with a thioacid of general formula R'COSH wherein R' is such that R'CO=R, except when R=H, at a temperature comprised between about the room temperature and about 80° C. for a time period comprised between about 24 hours and about 72 hours, thus obtaining a thiocarnitine of general formula (I) wherein R has the previously specified meaning with the exclusion of R=H;
(b) optionally, if thiocarnitine halogenide

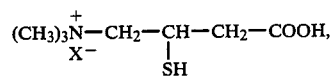

(R=H) is desired as end product, hydrolyzing the thiocarnitine of step (a) in an acid environment.

10. An orally or parenterally administerable pharmaceutical composition for protection against X-ray exposure, cutaneous regeneration from burns, facilitation of alcohol metabolism and use as alcohol detoxicants of the liver which comprises:

(a) a therapeutically effective amount of a thiocarnitine of the formula (I)

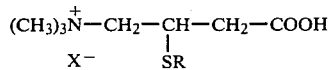

wherein:
X$^-$ is a pharmacologically acceptable halogenide ion, preferably the chloride ion, and
R is either hydrogen or the alkanoyl of a saturated organic acid having from 2 to 10 carbon atoms, and (b) a pharmaceutically acceptable exipient.

* * * * *